United States Patent [19]

Kitahara et al.

[11] Patent Number: 4,622,066
[45] Date of Patent: Nov. 11, 1986

[54] FLUORINE-CONTAINING BENZOPHENONE DERIVATIVES

[75] Inventors: Katsuhiko Kitahara, Kyoto; Tetsuya Masutani, Osaka; Takashi Yamaoka, Kusatsu; Tetsuo Kitahaba, Settsu; Takasi Nisioka, Sakai; Yasuo Itami, Higashi-Osaka, all of Japan

[73] Assignee: Daikin Kogyo Co., Ltd., Osaka, Japan

[21] Appl. No.: 569,734

[22] Filed: Jan. 10, 1984

[30] Foreign Application Priority Data

Jan. 12, 1983 [JP] Japan .................................. 58-4010

[51] Int. Cl.$^4$ ............... A01N 31/00; C07C 69/76; C07C 49/76
[52] U.S. Cl. .......................................... 71/98; 71/106; 71/107; 71/123; 560/24; 560/27; 560/52; 560/140; 568/22; 568/306; 568/319; 568/332; 568/333
[58] Field of Search .................. 71/122, 98, 106, 107, 71/123; 560/24, 27, 52, 140; 568/22, 306, 319, 332, 333

[56] References Cited

U.S. PATENT DOCUMENTS 3,954,875 5/1976 Swithenbank ........................ 71/123
4,120,687 10/1978 Meisenger ............................ 71/123

FOREIGN PATENT DOCUMENTS 0002666 7/1979 European Pat. Off.

Primary Examiner—Paul J. Killos
Attorney, Agent, or Firm—Birch, Stewart, Kolasch & Birch

[57] ABSTRACT

A fluorine-containing benzophenone derivative of the formula:

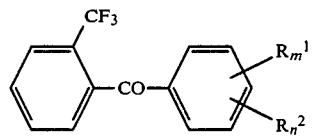

wherein $R^1$ is a group of the formula: —OM (in which M is hydrogen or alkali metal), lower alkoxy, lower acyloxy, a group of the formula:

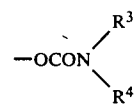

(in which $R^3$ and $R^4$ are same or different and hydrogen or lower alkyl) or a group of the formula: —OCH$_2$COOR$^5$ (in which $R^5$ is hydrogen, lower alkyl or alkali metal); $R^2$ is halogen, nitro, chlorosulfonyl, sulfo, trifluoromethyl or a group of the formula: —SCF$_2$H; and m and n are each an integer of 1 to 4 provided that the sum of m and n is not more than 5 having selective herbicidal activities on grasses and crops.

14 Claims, No Drawings

FLUORINE-CONTAINING BENZOPHENONE DERIVATIVES

The present invention relates to fluorine-containing benzophenone derivatives. More particularly, it relates to 2-trifluoromethylbenzophenone derivatives, a process for preparing the same and a herbicidal composition comprising the same.

Herbicidal benzophenones are disclosed in U.S. Pat. No. 3,954,875, Japanese Patent Publication No. 5446/1976 and Japanese Patent Publication (unexamined) (KOKAI) No. 2323/1979. However, these benzophenones have comparatively low herbicidal activities and are not satisfactory for practical use.

As a result of extensive study on a series of benzophenone derivatives having a trifluoromethyl group at the 2-position on one benzene ring, it has now been found that certain specific 2-trifluoromethylbenzophenone derivatives have selective herbicidal activities, namely that they have a strong and wide range of herbicidal activity on rice grasses and various wide-leave grasses while they are substantially harmless to crops such as soy bean, corn and cotton.

Accordingly, the present invention provides a fluorine-containing benzophenone derivative of the formula:

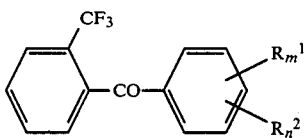
(I)

wherein $R^1$ is a group of the formula: —OM (in which M is hydrogen or alkali metal), lower alkoxy, lower acyloxy, a group of the formula:

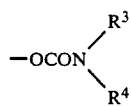

(in which $R^3$ and $R^4$ are same or different and hydrogen or lower alkyl) or a group of the formula: —OCH$_2$COOR$^5$ (in which $R^5$ is hydrogen, lower alkyl or alkali metal); $R^2$ is halogen, nitro, chlorosulfonyl, sulfo, trifluoromethyl or a group of the formula: —SCF$_2$H; and m and n are each an integer of 1 to 4 provided that the sum of m and n is not more than 5. When n is more than 1, the $R^2$ groups may be the same or different.

The terms lower alkyl, alkoxy and acyloxy herein used are intended to mean those having 1 to 8 carbon atoms, preferably 1 to 5 carbon atoms.

In comparison with conventional benzophenones, the characteristics of the fluorine-containing benzophenone derivative (I) are (1) that it has a trifluoromethyl group at the ortho-position on one benzene ring, and (2) that on the other benzene ring, it has at least one group $R^1$ which is a hydroxy group or a group derived therefrom and at least one electron attractive group $R^2$.

Specific examples of the fluorine-containing benzophenone derivatives (1) and their corresponding melting point are as follows:

(1) 2-trifluoromethyl-3'-chloro-4'-methoxybenzophenone (106°–8° C.)
(2) 2-trifluoromethyl-3',5'-dichloro-4'-methoxybenzophenone (103°–4° C.)
(3) 2-trifluoromethyl-3'-chloro-4'-methoxy-5'nitrobenzophenone (93°–94.5° C.)
(4) 2-trifluoromethyl-3'-chlorosulfonyl-4'methoxybenzophenone (97°–98.5° C.)
(5) 2,3'-di(trifluoromethyl)-4'-methoxy-5'-chlorobenzophenone (64°–5° C.)
(6) 2,3'-di(trifluoromethyl)-4'-methoxy-5'-sulfobenzophenone (98°–100° C.)
(7) 2,3'-di(trifluoromethyl)-4'-methoxy-5'-nitrobenzophenone (92°–3° C.)
(8) 2-trifluoromethyl-3'-nitro-4'-methoxybenzophenone (108°–110° C.)
(9) 2-trifluoromethyl-3',5'-dinitro-4'-methoxybenzophenone (122°–4° C.)
(10) 2-trifluoromethyl-3'-chloro-4'-hydroxybenzophenone (167°–9° C.)
(11) 2-trifluoromethyl-3',5'-dichloro-4'-hydroxybenzophenone (183°–4° C.)
(12) 2-trifluoromethyl-3'-chloro-4'-hydroxy-5'-nitrobenzophenone (186°–7° C.)
(13) 2-trifluoromethyl-3',5'-dinitro-4'-hydroxybenzophenone (98°–100° C.)
14) 2-trifluoromethyl-3'-nitro-4'-hydroxybenzophenone (74°–6° C.)
(15) 2-trifluoromethyl-3',5'-dichloro-4'-acetoxybenzophenone (119°–20° C.)
(16) 2-trifluoromethyl-3'-chloro-4'-(N,N-dimethylcarbamoyl)benzophenone (75°–6° C.)
(17) 2-fluoromethyl-3',5'-dichloro-4'-(N,N-dimethylcarbamoyl)benzophenone (97°–9° C.)
(18) ethyl 2-chloro-4-(2-trifluoromethylbenzoyl)-phenoxyacetate (88°–90° C.)
(19) sodium 2,6-dichloro-4-(2-trifluoromethylbenzoyl)phenolate (>300° C.)
(20) potassium 2,6-dichloro-4-(2-trifluoromethylbenzoyl)phenolate (>300° C.)
(21) 2-trifluoromethyl-3'-chloro-5'-fluoro-4'-hydroxybenzophenone (150°–2° C.)
(22) sodium 2-chloro-6-fluoro-4-(2-trifluoromethylbenzoyl)phenolate(>300° C.)
(23) 2-trifluoromethyl-3'-methyl-5'-nitro-4'-hydroxybenzophenone (104°–5° C.)
24) sodium 2-methyl-6-nitro-4-(2-trifluoromethylbenzoyl)phenolate (194° C.)
(25) 2-trifluoromethyl-3'-ethyl-5'-nitro-4'-hydroxybenzophenone (73°–4° C.)
(26) 2-trifluoromethyl-3'-n-propyl-5'-nitro-4'-hydroxybenzophenone (45°–6° C.)
(27) 2-trifluoromethyl-3'-isopropyl-5'-nitro-4'-hydroxybenzophenone (49°–50° C.)

The fluorine-containing benzophenone derivative (I) is prepared by, for example, reacting 2-trifluoromethylbenzoic acid or its chloride of the formula:

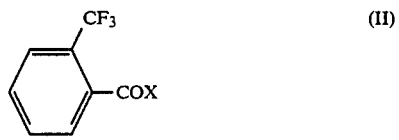
(II)

wherein X is hydroxy or chloro with a substituted benzene compound of the formula:

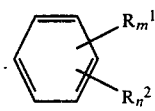

(III)

wherein $R^1$, $R^2$, m and n are the same as defined above in the presence of polyphosphoric acid or ferric chloride according to the Friedel-Crafts reaction. The reaction conditions may be conventional. For example, when polyphosphoric acid is used the reaction temperature is from 90° to 120° C. and the reaction time is from 3 to 6 hours. When ferric chloride is used, the reaction temperature is from 0° to 50° C. and the reaction time is from 0.5 to 5 hours. The fluorine-containing benzophenone derivative (I) wherein $R^2$ is nitro is prepared by nitrating the thus prepared benzophenone derivative with a mixture of nitric acid and sulfuric acid according to a per se conventional method.

The fluorine-containing benzophenone derivative (I) wherein $R^2$ is chlorosulfony or sulfo is prepared by sulfonating the thus prepared benzophenone derivative with chlorosulfonic acid.

The polychlorobenzophenone derivative (I) is prepared by chlorinating the benzophenone derivative obtained by the Friedel-Crafts reaction as described above with chlorine gas in the presence of ferric chloride.

The fluorine-containing benzophenone derivative (I) according to the present invention is useful not only as a herbicide but also as a medicine or an agricultural chemical such as a plant growth regulator, a germicide, an antiinflammatory drug, etc. Further, it is useful as an intermediate in the production of these medicines or agricultural chemicals.

When the fluorine-containing benzophenone derivative (I) is used as a herbicide, it may be formulated in the form of an emulsifiable concentrate, wettable powder or granule together with an appropriate carrier.

Preferred examples of the carrier in the preparation of the herbicide are, as a solid carrier, clay, kaolin, diatomaceous earth, silica, calicium carbonate, etc.; and as a liquid carrier, benzene, xylene, alcohols (eg. methanol, ethanol, etc.), acetone, cyclohexanone, dimethylformamide, dimethylsulfoxide, vegetable oils, fatty acids and their esters and surfactants.

Further, the herbicidal composition can include other conventional additives such as a spreader, an emulsifier, a lubricant, a sticking agent, etc.

The herbicidal composition comprising the fluorine-containing benzophenone derivative (I) may contain an agricultural germicide, insecticide, nematicide, herbicide, plant growth regulator, soil conditioner, fertilizer, etc.

The present invention will be hereinafter explained further in detail by the following Examples, in which parts are by weight.

EXAMPLE 1

Preparation of 2-trifluoromethyl-3′,5′-dichloro-4′-hydroxybenzophenone (11)

To an ice-cooled mixture of ferric chloride (3.0 g, 0.018 mol) and o-trifluoromethylbenzoyl chloride (3.6 g, 0.017 mol), o-chloroanisole (2.5 g, 0.018 mol) was added and stirred at 5° C. for one hour and then at 20° C. for two hours. The reaction mixture was extracted with chloroform (100 ml). The organic layer was washed with 10% hydrochloric acid followed by saturated brine, and chloroform was evaporated off to give a crude crystalline product (4.5 g). Yield, 84.2%. In the solution of the crude product in carbon teterachloride (100 ml), ferric chloride (0.05 g, 0.0003 mol) was added and then chlorine gas was bubbled at a room temperature overnight. The resulting reaction mixture was extracted with chloroform (100 ml). The organic layer was washed with 10% hydrochloric acid followed by saturated brine, and chloroform was evaporated off to give a crude crystalline product (4.3 g). Yield, 86.1%. The crude product was added to ca. 55% hydroiodic acid (30 ml) and refluxed for 10 hours. After cooling, the mixture was extracted with ethyl ether (100 ml). The organic layer was decolored with a 20% aqueous solution of sodium thiosulfate and washed with water. The solvent was evaporated off to give a crude crystalline product, which was recrystallized from ethyl acetate to give the pure entitled compound (3.8 g). Melting point, 183°–4° C. Yield, 92.1%. Overall yield, 65.7%.

EXAMPLE 2

Preparation of ethyl 2-chloro-4-(2-trifluoromethylbenzoyl)phenoxyacetate (18)

To the intermediate compound, 2-trifluoromethyl3′-chloro- 4′-methoxybenzophenone (3.2 g, 0.010 mol) as obtained in Example 1, ca. 55% hydroiodic acid (30 ml) was added and refluxed for 10 hours. After cooling, the mixture was extracted with ethyl ether (100 ml). The organic layer was decolored with a 20% aqueous solution of sodium thiosulfate and washed with water. The solvent was evaporated off to give a crude crystalline product (2.6 g). Yield, 85.0%. A solution of the crude product in tetrahydrofuran (6 ml) was added in a suspension of sodium hydride (about 50% in oil, 0.5 g) in tetrahydrofuran (8 ml) at a room temperature and stirred gently for 30 minutes. Then, a solution of ethyl bromoacetate (1.7 g, 0.01 mol) in dimethyl formamide was added (8 ml) and stirred at 100° C. for three hours. Thereafter, the reaction mixture was extracted with ethyl ether (100 ml) and the extract was washed with water. Then, the solvent was evaporated off to give a crude crystalline product, which was recrystallized from benzene to give the pure entitled compound (2.9 g). Melting point, 88°–90° C. Yield, 86.7%. Overall yield, 73.7%.

EXAMPLE 3

Formulation of wettable powder

The compound (11) (25 parts), talc (65 parts) and monogen powder (10 parts) are mixed thoroughly in a mortar to give a homogeneous wettable powder.

EXAMPLE 4

Formulation of the emulsifiable concentrate

The compound (14) (20 parts), a mixture of same amount of benzene and xylene (70 parts) and polyoxyethylene octylphenol ether (10 parts) are mixed to give a homogeneous emulsifiable concentrate.

Experiments 1–13 and Comparative Experiments 1–7

Plastic-made cups each having an inner diameter of 12 cm and a height of 7 cm were filled with a homogeneous mixture of granite-origin soil (80 parts) and a mixture of the same amount of organic substance-containing soil and compost (20 parts). The individual cups were seeded with ten seeds of *Oryza sativa, Echinochloa frumentacea, Digitaria adscendens, Medicago sativa, Brassica campestris* and *Brassica rapa* and top dressed with fine powdery soil with 0.3 mm thick. The cups were treated with a varying rate of the compound to be tested and kept in a green house for 40 days. Thereafter, the degrees of herbicidal activities of the compounds were determined by visual examination using a rating scale of 0 to 5 as follows:

5 Substantially all withered
4 Severly injured
3 Badly injured
2 Fairly injured
1 Slightly injured
0 Not injured The results are shown in Table 1.

The same experiments were carried out on comparative compounds. Their results are shown in Table 2.

TABLE 1

| Experiment No | Compound | Applied rate (Kg/ha) | Gramineae Oryza sativa | Gramineae Echinochloa frumentacea | Gramineae Digitaria adscendens | Leguminosae Medicago sativa | Cruciferae Brassica campestris | Cruciferae Brassica rapa |
| --- | --- | --- | --- | --- | --- | --- | --- | --- |
| 1 | Compound (3) | 10 | 0 | 2 | 4 | 0 | 1 | 1 |
|   |   | 3 | 0 | 0 | 4 | 0 | 0 | 1 |
|   |   | 1 | 0 | 0 | 2 | 0 | 0 | 0 |
| 2 | Compound (11) | 10 | 5 | 5 | 5 | 5 | 5 | 5 |
|   |   | 3 | 5 | 5 | 5 | 5 | 5 | 5 |
|   |   | 1 | 5 | 5 | 5 | 4 | 5 | 5 |
|   |   | 0.3 | 5 | 5 | 5 | 2 | 3 | 4 |
| 3 | Compound (10) | 10 | 5 | 5 | 5 | 5 | 5 | 5 |
|   |   | 3 | 5 | 5 | 4 | 3 | 5 | 5 |
|   |   | 1 | 5 | 5 | 4 | 3 | 4 | 5 |
| 4 | Compound (14) | 10 | 5 | 5 | 5 | 5 | 5 | 5 |
|   |   | 3 | 5 | 5 | 5 | 5 | 5 | 5 |
|   |   | 1 | 5 | 5 | 5 | 3 | 4 | 4 |
| 5 | Compound (15) | 10 | 5 | 5 | 5 | 5 | 5 | 5 |
|   |   | 3 | 5 | 5 | 5 | 5 | 5 | 5 |
|   |   | 1 | 4 | 4 | 5 | 3 | 3 | 3 |
| 6 | Compound (16) | 10 | 0 | 5 | 5 | 0 | 1 | 2 |
|   |   | 3 | 0 | 5 | 3 | 0 | 0 | 1 |
|   |   | 1 | 0 | 3 | 2 | 0 | 0 | 0 |
| 7 | Compound (18) | 10 | 5 | 5 | 5 | 4 | 5 | 5 |
|   |   | 3 | 3 | 5 | 4 | 1 | 3 | 5 |
|   |   | 1 | 2 | 4 | 3 | 0 | 2 | 4 |
| 8 | Compound (19) | 10 | 5 | 5 | 5 | 5 | 5 | 5 |
|   |   | 3 | 5 | 5 | 5 | 5 | 5 | 5 |
|   |   | 1 | 5 | 5 | 5 | 4 | 5 | 5 |
| 9 | Compound (21) | 10 | 5 | 5 | 5 | 5 | 5 | 5 |
|   |   | 3 | 5 | 5 | 5 | 5 | 5 | 5 |
|   |   | 1 | 5 | 5 | 5 | 5 | 5 | 5 |
|   |   | 0.3 | 5 | 5 | 5 | 4 | 4 | 5 |
| 10 | Compound (22) | 10 | 5 | 5 | 5 | 5 | 5 | 5 |
|   |   | 3 | 5 | 5 | 5 | 5 | 5 | 5 |
|   |   | 1 | 5 | 5 | 5 | 5 | 5 | 5 |
|   |   | 0.3 | 5 | 5 | 5 | 4 | 5 | 5 |
| 11 | Compound (23) | 10 | 5 | 5 | 5 | 5 | 5 | 5 |
|   |   | 3 | 5 | 5 | 5 | 3 | 5 | 5 |
|   |   | 1 | 5 | 5 | 3 | 2 | 5 | 5 |
|   |   | 0.3 | 4 | 4 | 3 | 1 | 3 | 5 |
| 12 | Compound (24) | 10 | 5 | 5 | 5 | 5 | 5 | 5 |
|   |   | 3 | 5 | 5 | 5 | 4 | 5 | 5 |
|   |   | 1 | 5 | 5 | 4 | 2 | 5 | 5 |
|   |   | 0.3 | 5 | 5 | 3 | 2 | 4 | 5 |
| 13 | Compound (27) | 10 | 5 | 5 | 5 | 5 | 5 | 5 |
|   |   | 3 | 5 | 5 | 4 | 3 | 5 | 5 |
|   |   | 1 | 4 | 4 | 3 | 2 | 4 | 5 |
|   |   | 0.3 | 4 | 4 | 3 | 1 | 3 | 4 |

TABLE 2

| Comparative Experiment No. | Comparative compound | Applied rate (Kg/ha) | Gramineae Oryza sativa | Gramineae Echinochloa frumentacea | Gramineae Digitaria adscendens | Leguminosae Medicago sativa | Cruciferae Brassica campestris | Cruciferae Brassica rapa |
| --- | --- | --- | --- | --- | --- | --- | --- | --- |
| 1 | 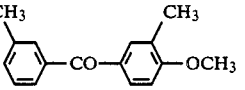 | 10 | 0 | 3 | 5 | 3 | 0 | 5 |
|   |   | 3 | 0 | 0 | 4 | 1 | 0 | 1 |
|   |   | 1 | 0 | 0 | 2 | 0 | 0 | 0 |

TABLE 2-continued

| Comparative Experiment No. | Comparative compound | Applied rate (Kg/ha) | Grass Gramineae Oryza sativa | Echinochloa frumentacea | Digitaria adscendens | Leguminosae Medicago sativa | Cruciferae Brassica campestris | Brassica rapa |
| --- | --- | --- | --- | --- | --- | --- | --- | --- |
| 2 | (pyrazole structure: CH₃, N-N-CH₃, CO-C₆H₃(Cl)(Cl), OSO₂-C₆H₄-CH₃) | 10 | 0 | 4 | 0 | 2 | 5 | 5 |
|  |  | 3 | 0 | 4 | 0 | 2 | 4 | 5 |
|  |  | 1 | 0 | 3 | 0 | 0 | 4 | 5 |
| 3 | 2-Cl-C₆H₄-CO-C₆H₂(Cl)(Cl)-OH | 10 | 5 | 5 | 5 | 5 | 5 | 5 |
|  |  | 3 | 5 | 5 | 4 | 5 | 5 | 5 |
|  |  | 1 | 4 | 4 | 2 | 2 | 4 | 4 |
|  |  | 0.3 | 2 | 1 | 0 | 0 | 1 | 3 |
| 4 | 2-CH₃-C₆H₄-CO-C₆H₂(Cl)(Cl)-OH | 10 | 4 | 5 | 4 | 5 | 5 | 5 |
|  |  | 3 | 3 | 5 | 2 | 3 | 4 | 5 |
|  |  | 1 | 2 | 3 | 1 | 2 | 2 | 3 |
|  |  | 0.3 | 0 | 0 | 0 | 0 | 0 | 1 |
| 5 | 2-CF₃-C₆H₄-CO-C₆H₃(Cl)-Cl | 10 | 0 | 1 | 0 | 2 | 0 | 0 |
|  |  | 3 | 0 | 0 | 0 | 0 | 0 | 0 |
|  |  | 1 | 0 | 0 | 0 | 0 | 0 | 0 |
| 6 | 2-CF₃-C₆H₄-CO-C₆H₃(NO₂)-Br | 10 | 0 | 0 | 0 | 0 | 0 | 0 |
|  |  | 3 | 0 | 0 | 0 | 0 |  | 0 |
|  |  | 1 | 0 | 0 | 0 | 0 | 0 0 | 0 |
| 7 | 2-CF₃-C₆H₄-CO-C₆H₃(CH₃)-OH | 10 | 0 | 1 | 3 | 1 | 2 | 1 |
|  |  | 3 | 0 | 0 | 2 | 0 | 1 | 0 |
|  |  | 1 | 0 | 0 | 0 | 0 | 0 | 0 |

Experiments 14–15 and Comparative Experiments 8–10

Unglazed pots each having an inner diameter of 20 cm were filled with soil sieved with a 4,000 mesh sieve and saturated with water.

The surface of the soil was seeded with seeds of grasses as shown in Tables 3 and 4, and top covered with fine soil. In each pot, seeds of soybean, cotton and corn as the crops were seeded 2 to 3 cm below the surface.

The pots were treated with a varying rate of the compounds to be tested and kept in a green house with watering every three days for 30 days. The herbicidal activities on the grasses were evaluated in the same manner as above. The height of the crops was measured and compared to that of the crops grown in untreated pots to determine the degree of the harmful effects on the crops.

The results are shown in Tables 3 and 4.

When the crops were treated with the fluorine-containing benzophenone derivatives according to the present invention, symptoms such as curling or shrinkage of the leaves were not observed.

Experiments 16–18 and Comparative Experiments 11–12

Soil of a rice field was filled in 1/5,000 are of wagner pots, mixed with water thoroughly and filled with water so that the surface of the soil was covered with water. The surface of the soil was smoothed and rice seedlings of three-leaf stage were transplanted 2 to 3 cm below the surface. Simultaneously, seeds of *Panicum crusgalli*, *Scirpus juncoides* and *Cyperus difformis* were seeded and tubers of *Sagittaris pygmaea* and *Cyperes serotinus* were placed. The pots were treated with a varying rate of the compounds to be tested and the water depth was kept to 3 cm. The pots were kept in a green house at a temperature of from 20° to 30° C. for one month after treatment with the compounds. The herbicidal activities on the grasses were evaluated in the same manner as above and the phytotoxic effects on the rice plants were determined by visual examination using the following rating scale:

| | |
| --- | --- |
| ++++ | Substantially all withered |
| +++ | Severly injured |
| ++ | Badly injured |
| + | Fairly injured |
| ± | Slightly injured |
| − | Not injured |

The results are shown in Table 5.

TABLE 3

| Compound | Applied rate (g/a) | Herbicidal activity | | | | | Phytotoxic effect (%) | | |
|---|---|---|---|---|---|---|---|---|---|
| | | Monocotyledoneae | | Dicotyledoneae | | | Glycine max | Gossypium | Zea mays |
| | | Echinochloa frumentacea | Digitaria adscendens | Polygonum sp. | Ipomoea purpurea | Cyperus rotundus L. | | | |
| (Experiment 14) | 15 | 5 | 5 | 2 | 3 | 0 | 83 | 90 | 85 |
| Compound (11) | 5 | 5 | 5 | 0 | 1 | 0 | 61 | 102 | 81 |
| | 1.5 | 4 | 4 | 0 | 1 | 0 | 106 | 104 | 104 |
| (Comparative | 15 | 5 | 5 | 3 | 3 | 0 | 48 | 77 | 0 |
| Experiment 8) | 5 | 3 | 4 | 2 | 3 | 0 | 81 | 83 | 27 |
| TRIFLURALIN*[1] | 1.5 | 2 | 2 | 1 | 1 | 0 | 104 | 128 | 60 |
| | 0.5 | 0 | 1 | 0 | 1 | 0 | 83 | 101 | 96 |
| Non-treated | — | 0 | 0 | 0 | 0 | 0 | 100 | 100 | 100 |

Note:
*[1] 2,6-dinitro-N,N—dipropyl-4-trifluoromethylaniline

TABLE 4

| Compound | Applied rate (g/a) | Herbicidal activity | | | | | | Phytotoxic effect (%) | | |
|---|---|---|---|---|---|---|---|---|---|---|
| | | Monocotyledoneae | | | | Dicotyledoneae | | Glycine max | Gossypium | Zea mays |
| | | Echinochloa frumentacea | Digitaria adscendens | Setaria crus-galli | Cyperus defformis | Plantago major | Rumex japonicus | | | |
| (Experiment 15) | 15 | 5 | 5 | 5 | 5 | 5 | 0 | 79 | 108 | 91 |
| Compound (11) | 5 | 5 | 5 | 5 | 5 | 5 | 0 | 103 | 109 | 84 |
| | 1.5 | 4 | 4 | — | — | — | 0 | 83 | 102 | 106 |
| | 0.5 | 2 | 3 | — | — | — | 0 | 91 | 111 | 94 |
| (Comparative | 15 | 5 | 5 | 5 | 5 | 5 | 0 | 79 | 90 | 87 |
| Experiment 9) | 5 | 5 | 5 | 4 | 5 | 4 | 0 | 113 | 111 | 106 |
| ALACHLOR*[1] | 1.5 | 4 | 4 | — | — | — | 0 | 95 | 85 | 82 |
| | 0.5 | 1 | 1 | — | — | — | 0 | 111 | 113 | 97 |
| (Comparative | 15 | 5 | 4 | 4 | 5 | 5 | — | 101 | 100 | 111 |
| Experiment 10) | 5 | 2 | 3 | 3 | 5 | 4 | — | 99 | 111 | 105 |
| BENTHIOCARB/ | 1.5 | 1 | 1 | — | — | — | — | 107 | 92 | 97 |
| PROMETRYNE*[2] | 0.5 | 0 | 0 | — | — | — | — | 114 | 127 | 135 |
| Non-treated | — | 0 | 0 | 0 | 0 | 0 | 0 | 100 | 100 | 100 |

Note:
*[1] 2-chloro-2',6'-diethyl-N—methoxymethylacetoanilido
*[2] Emulsion containing 50% of S—(4-chlorobenzyl)-N,N—diethylthiocarbamate and 5% of 2,4-bisisopropylamino-6-methylthio-1,3,5-triazine

TABLE 5

| Compound | Applied rate (g/a) | Herbicidal activity | | | | Phytotoxic effects |
|---|---|---|---|---|---|---|
| | | Panicum crus-galli | Sagittaria pygmaea | Cyperes serotinus | Scirpus juncoides | Rice plant |
| (Experiment 16) | 100 | 5 | 5 | 5 | 5 | + |
| | 30 | 5 | 5 | 5 | 5 | ± |
| Compound (11) | 10 | 5 | 2 | 5 | 5 | — |
| | 3 | 5 | 0 | 2 | 5 | — |
| (Experiment 17) | 100 | 5 | 5 | 5 | 5 | ± |
| | 30 | 4 | 4 | 2 | 5 | — |
| Compound (14) | 10 | 4 | 0 | 0 | 2 | — |
| | 3 | 3 | 0 | 0 | 1 | — |
| (Experiment 18) | 100 | 5 | 5 | 5 | (5) | ± |
| | 30 | 5 | 4 | 5 | (5) | — |
| Compound (23) | 10 | 5 | 2 | 5 | (5) | — |
| | 3 | (5) | (1) | (4) | (5) | |
| (Comparative Experiment 11) Cl–⌬–CO–⌬(NO₂)–OH | 100 | 5 | 3 | 2 | 5 | — |
| | 30 | 3 | 1 | 2 | 4 | — |
| | 10 | 0 | 0 | 0 | 0 | — |
| | 3 | 0 | 0 | 0 | 0 | — |
| (Comparative Experiment 12) CH₃–⌬–CO–⌬(CH₃)–OCH₃ | 100 | (5) | (3) | (4) | (5) | (+) |
| | 30 | 5 | 2 | 3 | 5 | ± |
| | 10 | 3 | 0 | 0 | 3 | — |
| | 3 | (1) | (0) | (O) | (0) | — |

What is claimed is:
1. A fluorine-containing benzophenone derivative of the formula:

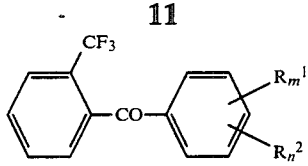

wherein $R^1$ is a group of the formula: —OM (in which M is hydrogen or alkali metal), lower acyloxy, a group of the formula:

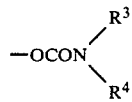

(in which $R^3$ and $R^4$ are same or different and hydrogen or lower alkyl) or a group of the formula: —OCH$_2$COOR$^5$ (in which $R^5$ is hydrogen, lower alkyl or alkali metal); $R^2$ is a lower alkyl group, halogen, nitro, chlorosulfonyl, sulfo, trifluoromethyl or a group of the formula: —SCF$_2$H; and m and n are each an integer of 1 to 4 provided that the sum of m and n is not more than 5.

2. The fluorine-containing benzophenone derivative according to claim 1, wherein $R^1$ is the group of the formula: —OM in which M is the same as defined above.

3. A fluorine-containing benzophenone derivative according to claim 1, wherein $R^1$ is lower acyloxy.

4. A fluorine-containing benzophenone derivative according to claim 1, wherein lower acyloxy is acetoxy.

5. A fluorine-containing benzophenone derivative according to claim 1, wherein $R^1$ is the group of the formula

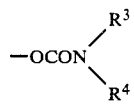

in which $R^3$ and $R^4$ are the same as defined above.

6. A fluorine-containing benzophenone derivative according to claim 1, wherein $R^2$ is a halogen atom.

7. A fluorine-containing benzophenone derivative according to claim 1, wherein the halogen atom is fluorine or chlorine.

8. A fluorine-containing benzophenone derivative according to claim 1, wherein $R^2$ is a lower alkyl group.

9. A fluorine-containing benzophenone derivative according to claim 8, wherein lower alkyl group is a member selected from the group consisting of methyl, ethyl, propyl and butyl.

10. A fluorine-containing benzophenone derivative according to claim 1, wherein $R^2$ is the group of the formula: —OCH$_2$COOR$^5$ in which $R^5$ is the same as defined above.

11. A herbicidal composition comprising, as an active ingredient, a fluorine-containing benzophenone derivative of the formula:

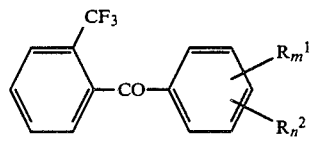

wherein $R^1$ is a group of the formula: —OM (in which M is hydrogen or alkali metal), lower acyloxy, a group of the formula:

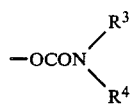

(in which $R^3$ and $R^4$ are same or different and hydrogen or lower alkyl) or a group of the formula: —OCH$_2$COOR$^5$ (in which $R^5$ is hydrogen, lower alkyl or alkali metal); $R^2$ is a lower alkyl group, halogen, nitro, chlorosulfonyl, sulfo, trifluoromethyl or a group of the formula: —SCF$_2$H; and m and n are each an integer of 1 to 4 provided that the sum of m and n is not more than 5.

12. A herbicidal composition according to claim 11, which is in the form of an emulsifiable concentrate.

13. A herbicidal composition according to claim 11, which is in the form of wettable powder.

14. A herbicidal composition according to claim 11, which is in the form of granule.

* * * * *